United States Patent [19]
Lajus et al.

[11] 3,936,642
[45] Feb. 3, 1976

[54] X-RAY FILM-HANDLING ARRANGEMENT FOR X-RAY DIAGNOSTIC APPARATUS

[75] Inventors: Pierre Lajus; Edmond Chambron, both of Paris, France

[73] Assignee: Compagnie Generale de Radiologie, Paris, France

[22] Filed: Oct. 9, 1974

[21] Appl. No.: 513,510

[30] Foreign Application Priority Data
Oct. 12, 1973 France .......................... 73.36608

[52] U.S. Cl. .............................................. 250/469
[51] Int. Cl.² .......................................... G11B 1/00
[58] Field of Search ........................... 250/468, 469

[56] References Cited
UNITED STATES PATENTS
3,488,469   1/1970   Schneeman ........................ 250/469
FOREIGN PATENTS OR APPLICATIONS
274,469   9/1970   U.S.S.R. .............................. 250/469

Primary Examiner—James W. Lawrence
Assistant Examiner—T. N. Grigsby
Attorney, Agent, or Firm—Cushman, Darby & Cushman

[57] ABSTRACT

An X-ray film-handling arrangement for taking X-ray photographs in which the length of the format is variable, including a movable leaded mask which may cover part of the exposure field and a device for feeding and transporting the film comprising conveyor belts and a so-called indexing belt provided with a marker, which reproduces the movement of the belts. When this marker passes in front of detectors attached to the end of the mask, it causes these to generate control signals which are fed respectively to a clutch and a brake, so as to stop the movement of belts when the film reaches the front end of mask.

5 Claims, 7 Drawing Figures

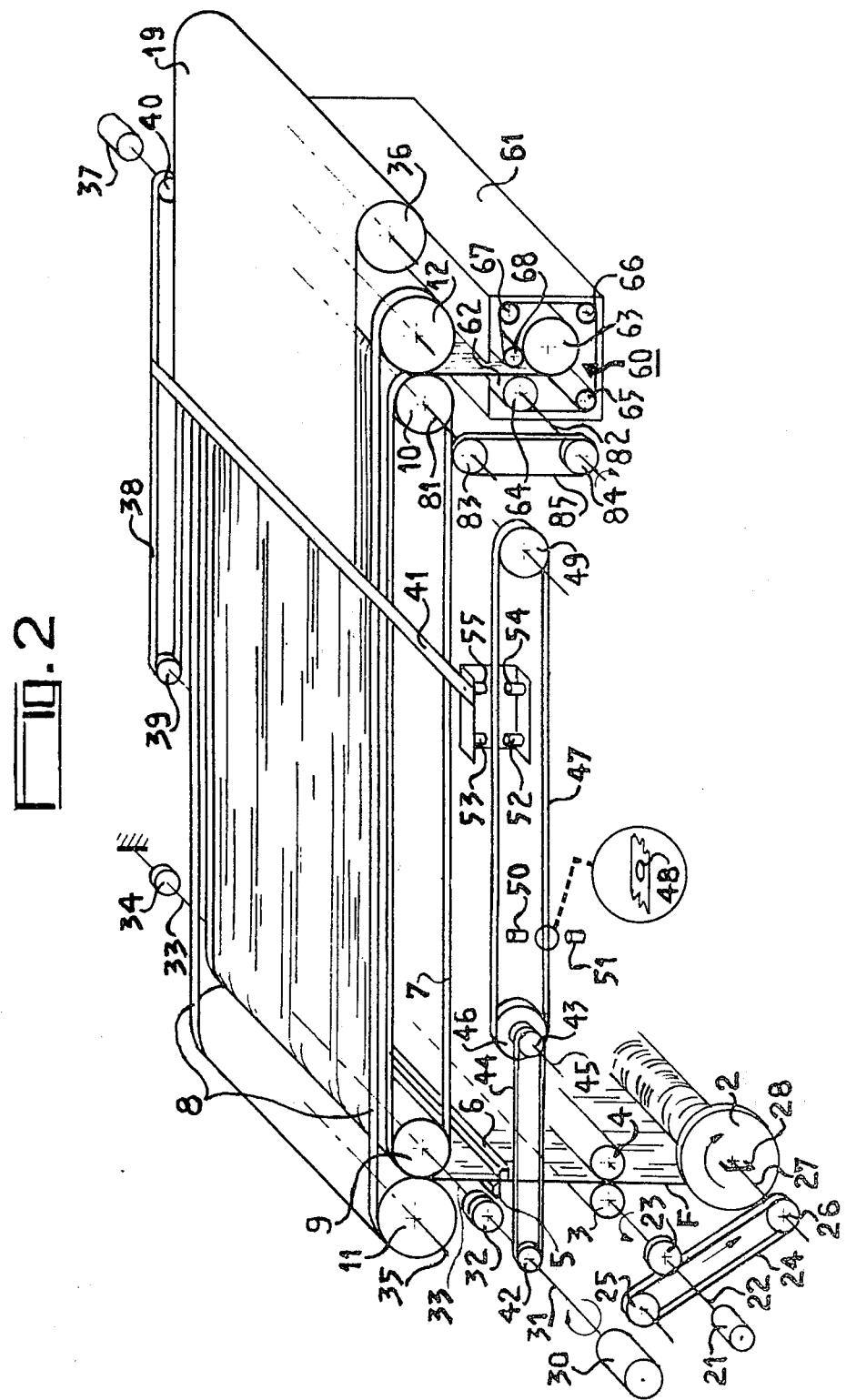

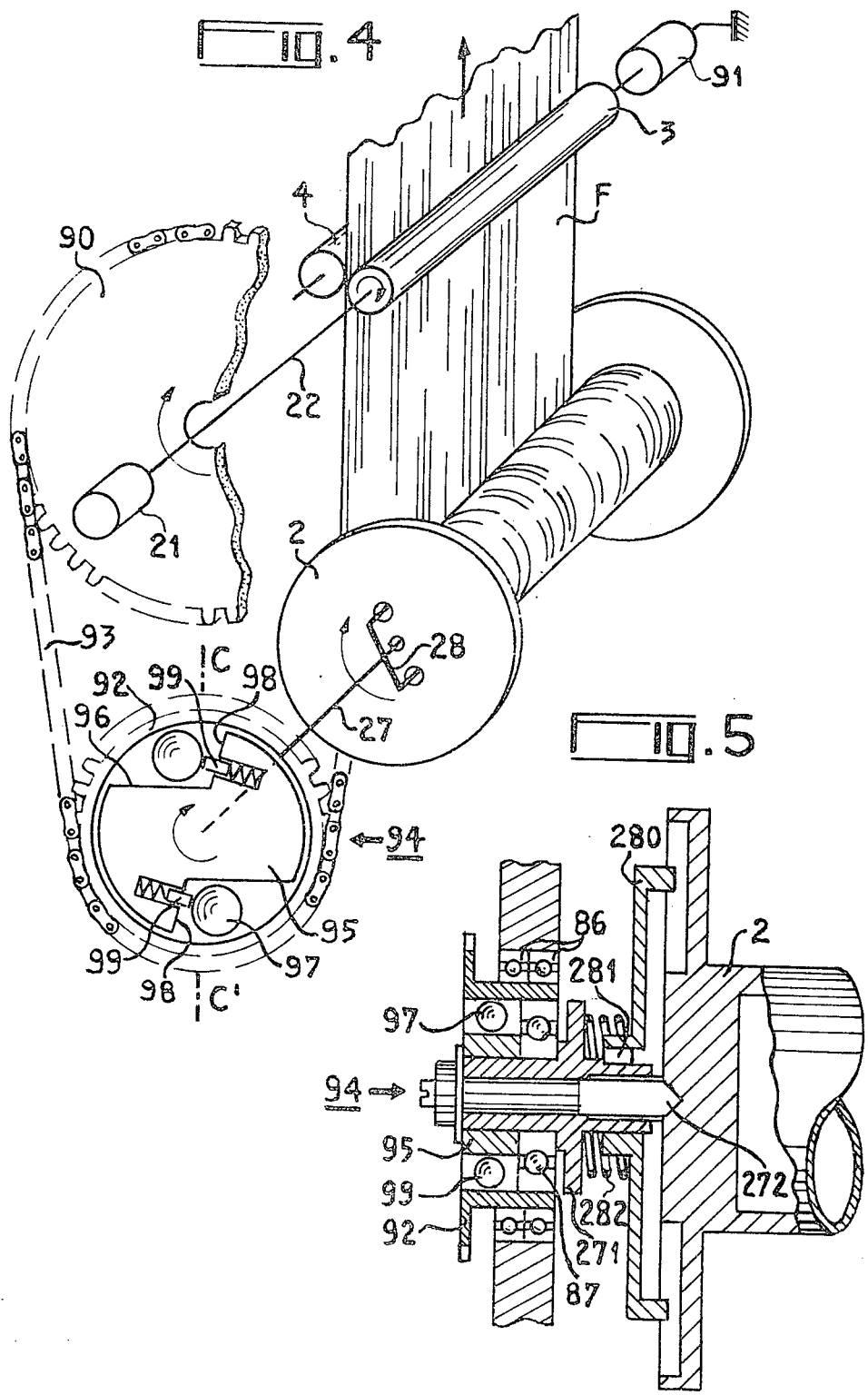

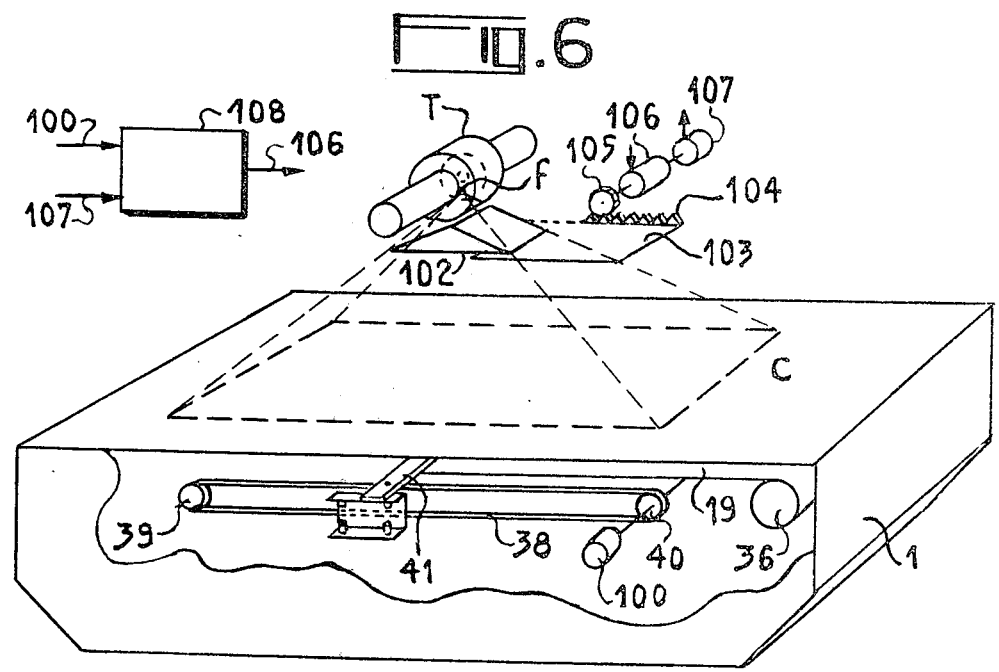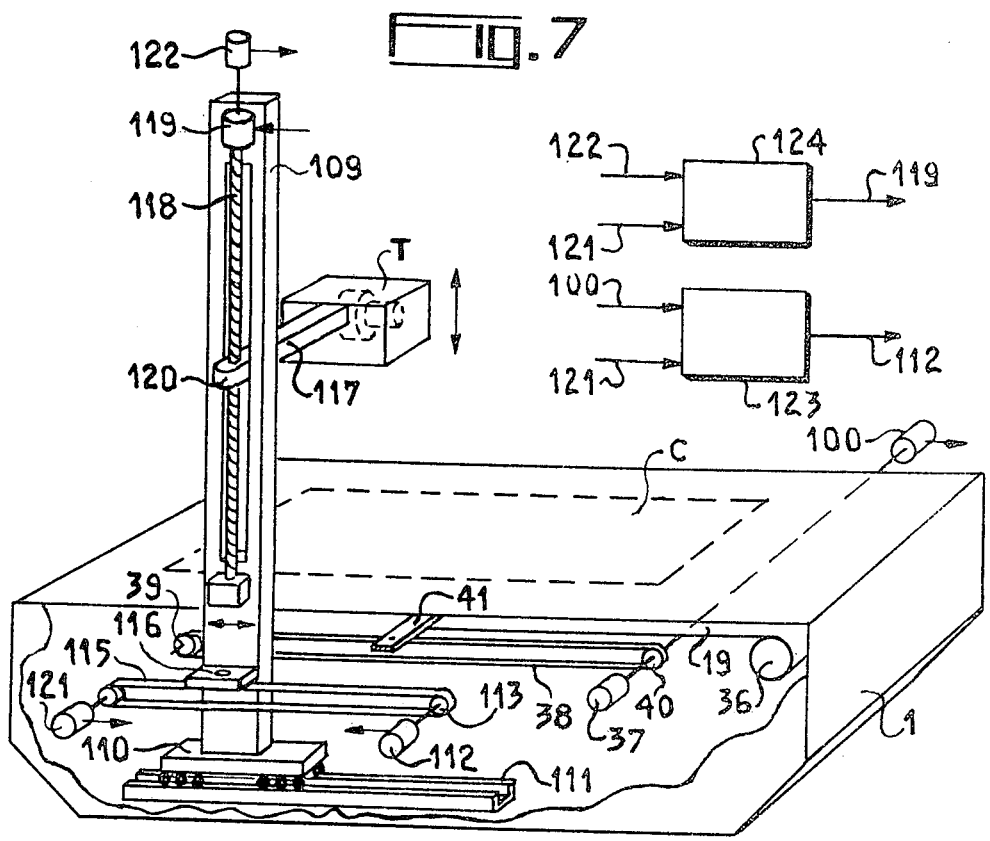

X-RAY FILM-HANDLING ARRANGEMENT FOR X-RAY DIAGNOSTIC APPARATUS

The present invention relates to X-ray film handling arrangements for taking X-ray photographs and to X-ray diagnostic apparatus incorporating such arrangements. It relates more particularly to arrangements and apparatus of this type, which facilitate X-ray examination of blood vessels using an injected contrast medium, such examinations being for example those of vascular tissue in the lower limbs (phlebography) which call for radiographs of considerable length.

In a prior art apparatus of this type, a film-changer supplies film with constant size and the arteriophlebography is carried out in stages, that is to say by means of a series of successive radiographs, either using the patient support plate to move the patient in relation to the assembly formed by the X-ray source and the image receiver (X-ray film or image intensifier), or by moving the source and image receiver assembly in relation to the plate, to two or more successive positions and then, once the radiographs have been developed, by juxtaposing them and fastening them together end to end to obtain an X-ray image of thee whole limb.

In another type of apparatus special cassettes are used whose format may vary to suit the photograph to be taken, but the maximum dimensions of such cassettes are once again limited in most cases and may not correspond to the size of the organ to be examined. In this case, besides making provision for relative movement between the patient and the source-image receiver assembly, it is generally necessary to provide a cassette-changing device which enables the exposed cassette to be replaced by an unused one, and also sets of special cassettes of various formats suitable for use with the equipment.

Because of the fact that all the photographs are not taken at the same time, prior art arrangements and apparatus, even when controlled by means of a programming device, do not give a vascular image which is true for one given instant in time. In addition, they call for delicate operations to be carried out in cutting, matching and joining the ends of photographs.

The arrangement and apparatus according to the present invention enables these drawbacks to be overcome. It is an object of the invention to provide an arrangement for obtaining an image of the way in which the contrast medium is distributed through blood vessels situated in large areas of the body, such as the lower limbs for example, at predetermined instants and in a single operation.

The X-ray film-handling arrangement according to the invention includes a tiltable table which enables examinations to be made in any position between the horizontal and the vertical, a film transfer device for film in rolls provided with an image intensifier and comprising feed members for the film to be transferred from a magazine containing the roll of film to the exposure field and into a predetermined position therein and then after exposure, to transfer the exposed film sheet to a storage magazine, the length of the film being continuously variable from approximately 0.4 meters up to 1.20 meters.

In accordance with the invention, there is provided an X-ray film handling arrangement for taking X-ray photographs including a feeding device which feeds out the film from the roll and consists of a first pair of contiguous feeder rollers driven by a first motor; a film transfer means including two pairs of flat, superimposed and contiguous conveyor belts which are respectively tended between a second and a third pair of feed rollers driven by a second motor, the two pairs of belts being located on said rollers in such a way as to grip the lateral edges of the film, said second motor having a shaft which is coupled to the shaft of at least one of the two contiguous feed rollers through a clutch, this shaft also being provided with a brake; a cutting device located between the feeding device and the transfer device for cutting the film after it has been positioned in the exposure field; and a movable member such as a leaded mask which is displaced by means of a third motor and which limits the length of film being irradiated to a predetermined length whatsoever between predetermined maximum and minimum sizes, is chiefly characterised by the fact that it further comprises an additional so-called indexing belt held in parallel with the conveyor belts by means of two pulleys which are located beyond respective extreme positions of the said movable member, one of said pulleys being coupled to the shaft of the second motor in such a way that a random point on the indexing belt reproduces the displacement of the film and is moved for a distance identical to the length of the film which is transferred by said conveyor belts, said indexing belt bearing a marker which co-operates with at least one detection device secured to the end of the said movable member, and located adjacent said indexing belt, said detection device supplying, when the said marker passes adjacent thereto, a control signal which is transmitted to the said clutch and/or brake, whereby to stop the movement of the conveyor belts transferring the film, when the end of the film reaches the movable member.

The invention will be better understood and others of its features and advantages will become apparent from the following description, given by way of example, and from the accompanying drawings relating thereto, in which:

FIG. 2 is a general schematic perspective view of the members for feeding and transfering the film in an arrangement according to the invention;

FIG. 4 is a schematic view of a device for unwinding the film which makes it possible to prevent the forming of a loop in the film;

FIG. 5 shows in cross-section a device for driving the film-spool; and

FIGS. 6 and 7 are schematic perspective views of the different embodiments of an X-ray diagnostic apparatus including an arrangement according to the invention.

In all the Figures corresponding elements are indicated with the same reference numeral.

FIG. 1 is a schematic cross-sectional view of a prior art film-changer handling device from which the arrangement according to the invention is derived.

Such a prior art handling device film preferably contains a combination of at least some of the elements described in U.S. Pat. Nos. 3,636,351; 3,710,106 and 3,775,613 assigned to the present assignee or British Patent Specifications Nos. 1,318,758; 1,311,593 and 1,367,414 granted to the applicant.

Figure 1:
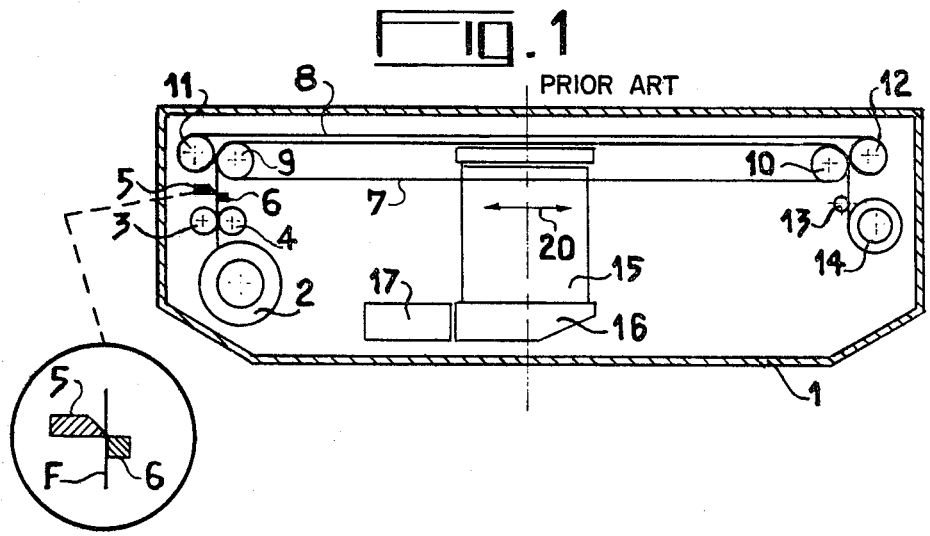
FIG. 1 is a schematic side-elevational view of the arrangement of a prior art X-ray film-handling device, one of the housing sidewalls being removed.

In FIG. 1, the prior art film-handling device contains, within a light-proof housing or casing 1, a magazine containing a roll of film F on a reel or spool 2, a first pair of contiguous feeding rollers 3, 4 to extract the film from the magazine, a cutting means consisting of a movable blade 5 and a fixed blade 6 which are orientated perpendicularly to the direction of movement of the film F and situated at the input to the means for transfering the film F. The cutter 5, 6 may be used to cut the film when it is in position for exposure. The transfer means consists mainly of two pairs of contiguous conveyor belts 7 and 8, the facing surfaces of which grip the edges of the film F so as to carry it along therewith. The lower belts 7 are tensioned by means of a second pair of rollers 9 and 10 and the upper belts 8 by means of a third pair of rollers 11 and 12. Rollers 9 and 11 are contiguous and are positioned in front of the exposure field so as to receive the film which is extracted from the magazine 2 by the first pair of rollers 3, 4 and to transfer it to the exposure field by means of the two pairs of conveyor belts 7, 8. Rollers 10 and 12 are likewise contiguous and are positioned beyond the exposure field so as to transfer the exposed film to a storage magazine which is represented here by a guide-roller 13 and a spool 14. The prior art exposure chamber also includes an image intensifier 15 followed by an optical device 16 and a television camera 17 so as to allow radioscopic examinations to be carried out.

In an X-ray film-handling arrangement according to the invention, the exposure field is of constant width and is of a length which can be varied starting from a fixed origin situated to the right of roller 9 and which is determined by the position of a movable leaded mask (see 19 in FIG. 2). Consequently the intensifier 15 should be movable in parallel to the movement of the film within this field, i.e. in the directions indicated by the double-headed arrow 20.

FIG. 2 is a schematic, perspective view of the mechanism for feeding and transfering the film and of the means for controlling the position of the film in the exposure field, in a X-ray film-handling arrangement according to the invention.

In FIG. 2, the first pair of contiguous rollers 3, 4 are driven by a first motor 21, the shaft 22 of which is secured to the shaft of roller 3, with roller 4 free to turn in bearings (not shown). The shaft 22 of motor 21 is also coupled to the spool 2 containing the reserve ot film by means of a special transmission which will be explained in more detail hereinafter (see FIGS. 4 and 5) and which is represented here by a belt 24 tended between two pulleys 25 and 26. The latter pulley 26 is carried by a shaft 27 which terminates at one end in a three-pronged fork 28 which engages in one of the cheeks of the spool 2. Against this tended belt 24 frictionally bears a pulley 23 which is secured to the shaft 22 of motor 21. The film F, driven by rollers 3, 4 is fed between the blades 5, 6 of the cutting means and on to the contiguous rollers 9 and 11 which carry the two pairs of conveyor belts 7 and 8 respectively. The film F is gripped along the edges between the two rollers 9 and 11 by the contiguous surfaces of the two pairs of belts 7 and 8 and is transported into the exposure field which may extend from the right-hand side of roller 9 to the left-hand side of roller 10.

The maximum extent of the exposure field is effectively determined by the dimensions of the intensifier screens (not shown in the figures) which in this case are mounted on two rectangular plates of constant thickness made of a material substantially transparent to X-rays and which are arranged on either side of the plane of the film as described in the aforementioned United States and British Patent Specifications.

The first plate, which carries the upper screen, is fixed with respect to the housing 1 (FIG. 1) and the second, which carries the lower screen, is supported by lift jacks so that it can be moved away from the plane of the film while the film is being transferred and can be brought to bear against the underside of the film while the photograph is being taken. In the arrangement according to the invention, the lower screen is carried by a set of eight jacks and, when the film is situated in the desired position, the screens are moved together firstly along one longitudinal edge and then by pivoting like a book in order to expel the air from between the two screens and the inserted film.

The conveyor belt assembly 7, 8 is driven by means of a second motor 30, the shaft 31 of which carries at its end a clutch 32 which allows it to be coupled to one end of the shaft 33 of roller 9. The other end of shaft 33 is connected to a brake 34 which is used to stop the mechanism for feeding the film F when the latter is in the desired position.

Shaft 35 of roller 11 may rotate freely and be driven by friction or may be coupled to shaft 33 in such a way as to drive the contiguous belts 7 and 8 at substantially the same speed.

The position of the film F in the exposure field, i.e. the length of the format, is determined by the position of a leaded mask 19 which is partly rigid and partly flexible, the flexible part being wound onto a roller 36 located beyond the exposure field. The position of the mask can be controlled by a third motor 37 which drives a pair of belts 38 (only one of which is shown here) which are arranged to either side of the conveyor belts 8 for placing the mask anywhere within the exposure field. Belts 38 are tensioned between two pairs of pulleys 39 and 40 one of which is situated at a position corresponding to the minimum length of film and the other of which is situated near the point at which the film leaves the exposure field. One of the pairs of pulleys 39, 40 is driven by the third motor 37. The free end of mask 19 is provided with a mechanically rigid strip 41 which is perpendicular to the belts 38 and is attached thereto.

The film-handling arrangement according to the invention further includes a so-called indexing means which allows the film to be stopped at the point where the strip 41 is situated. This indexing device is driven by the second motor 30 through a pulley 42 attached to shaft 31. The pulley 42 is coupled to another pulley 43 by a transmission belt 44. The shaft 45 of pulley 43 has secured to it an additional pulley 46 which drives an indexing belt 47. The indexing belt carries a marker 48 and reproduces the transfer cycle of the film, i.e. the marker 48 being displaced by the same amount as the film is, when clutch 32 connects shafts 31 and 33 together. The indexing belt 47 is tended between two pulleys 46 and 49, the latter of which is located substantially adjacent to film-transferring roller 10, since its position determines the maximum length of the film.

The distance between pulleys 46, 49 and their diameter i.e. the length of the indexing belt 47, is chosen so as to correspond very precisely to the length of the film between the point of contact with rollers 9 and 10 and the most remote position (adjacent to roller 10) of the strip 41. The marker 48 is formed, for example, by a hole made in the opaque belt 47. It must follow a path which takes it from a first fixed assembly formed by a source 50 and a detector 51 of a predetermined inactinic radiation which corresponds to the point of contact between rollers 9 and 10, to a similar second (52, 53) and third (54, 55) source and detector assembly which are mounted on the strip 41. Each of the source and detector assemblies consists of, for example a source of and a detector of inactinic (infra-red) radiation, which are aligned with each other on either side of the indexing belt 47. The marker 48 and the detectors 51, 53 and 55 may also be formed respectively by a cam, a stop or a finger, and contact-breakers or changeover switches which are operated by the passage of one of the former. Before the beginning of each transfer cycle, the marker 48 is stopped at a position where it allows radiation to pass between the first source 50 and the first detector 51, and the second motor 30 is stopped with the clutch 32 and the brake 34 engaged.

When the transfer cycle begins, clutch 32 remains in engagement, brake 34 is released, and the motor 30 is started, thus drawing the film between the conveyor belts 7 and 8 towards the strip 41, and the marker 48 of the indexing belt 47 towards the second 53 and then the third 55 detector.

When the marker 48 passes adjacent the second detector 53, the detector produces a first control signal which is applied to the clutch 32 to release it, brake 34 remaining released and motor 30 energised. This results in a slowing down of the movement of the conveyor belts 7, 8 and of the film F and as they are no longer driven by the second motor 30 and move only by their own inertia. However, motor 30 continues to drive the marker 48 towards the third detector 55 and when adjacent to the latter detectors delivers a second control signal which causes the brake 34 to be actuated so as to stop rollers 9 and 12 and conveyor belts 7 and 8 with the film level with rail 41. The second control signal from the third detector 55 may likewise bring into motion the pressure plate carrying the movable intensifying screen, which in turn may start up a high voltage generator supplying an X-ray tube for taking the photographs.

While brake 34 is applied and clutch 32 released, motor 30 continues to move the marker 48 of the indexing belt 47 to the starting position, and when this position is reached the first detector 51 delivers a third control signal which is used both to cut off the supply to motor 30 and to operate the clutch 32, which latter brakes shaft 31 so as to bring the marker 48 to a halt opposite detector 51.

The film is cut and thereafter transported to the storage magazine 60 (which will be described in greater detail hereinbelow) either each time a photographs is taken or after a series consisting of a predetermined number of photographs. In the first case, the cutter 56 is actuated either by the signal which third detector 55 delivers when the film is in position, or after the film has been exposed. When the cutter 5, 6 has finished cutting the film, brake 34 is released and motor 30 started up until the film is clear of the space between rollers 10 and 12 and the marker 48 has arrived opposite the first detector 51.

In the second case, the cutter 5, 6 may be operated only when the last photograph in a series has come into position, the previous photographs in the series being fed into the magazine 60 each time the film F is moved up.

Figure 3:
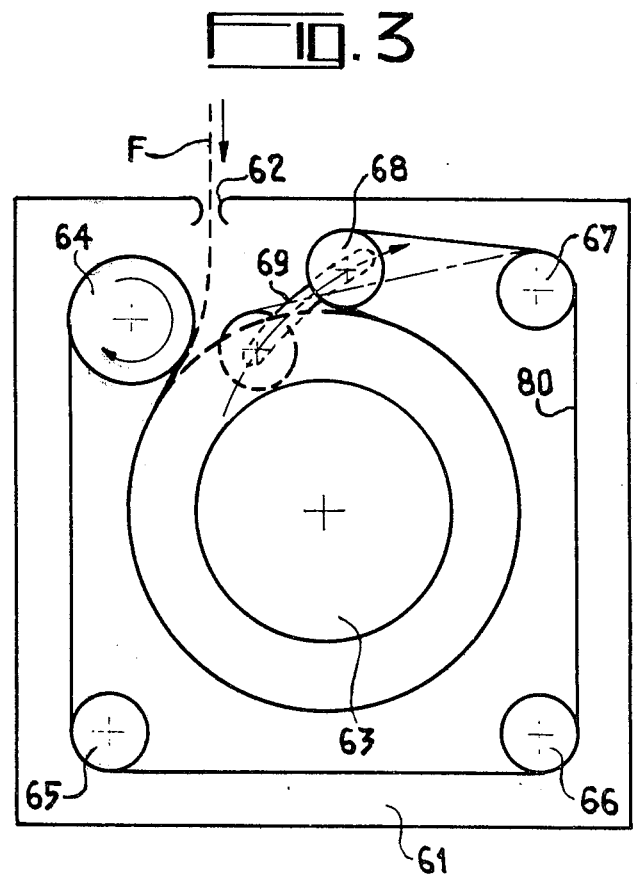
FIG. 3 is a schematic cross-sectional view of the magazine for storing the exposed photographs in an arrangement according to the invention.

The magazine 60, which is shown in greater detail in FIG. 3, consists of a parallelepiped light-proof casing 61 which has a slot 62 to allow the film F to pass through. Inside the casing 61 it contains: a central cylindrical roller 63 onto which the exposed film is wound, four peripheral rollers 64, 65, 66 and 67 arranged in respective corners of the casing 61, whose axes are parallel to that of the central roller 64 and which are mounted in bearings, fixed with respect to the casing 61, and a sixth roller 68 whose shaft is movably carried in a curved seating 69 and which is urged against the central roller 63 by elastic means (not shown). Two or more parallel belts 80 are passed around the central roller 63, with one of their faces touching the latter, and their other faces passing around the group of peripheral rollers 64, to 67 and the movable roller 68, so that the film F which enters the magazine 60 through the slot 62 is caught between the belts 80 and the central roller 63 and is wound around the latter.

All the magazine's rollers 63 to 68 are made to rotate by driving the first peripheral roller 64 which drives the belt 80 in such a way that these belts at least will move at substantially the same speed as that at which the film is moving as it leaves the two contiguous rollers 10 and 12 (in FIG. 2).

This is obtained (see FIG. 2) by coupling the shaft 81 of roller 10 to the shaft 82 of roller 64 by means of two pulleys 83 and 84 and a transmission belt 85 and by making the ratio between the diameters of pulleys 83 and 84 the inverse of that of the diameters of rollers 10 and 64.

FIG. 4 is a schematic view of a device for unrolling the film from spool 2 arranged to prevent loop formation.

In FIG. 4, the contiguous rollers 3 and 4 are used to extract the film from the spool 2 and to feed it to the conveyor belts of the transfering means described above (see FIGS. 1 and 2). The shaft of roller 3 is secured to the shaft 22 of the first motor 21 and this shaft also carries a sprocket-wheel 90 secured thereto and a brake 91. Sprocket-wheel 90 is coupled by a chain 93 to a peripheral sprocket-ring 92. The sprocket-ring 92 is driven by motor 21 and within its body there is arranged a coupling device for one way rotation, such as a ratchet-motion, a strut-action pawl-motion, or other irreversible coupling device 94 which employs strutting rolls or balls, connected to a shaft 27, which in turn is coupled to the spool 2 by fork 28. The direction of rotation permitted by the ratchet-motion 94 is opposite to that for which the film F is unrolled from the spool 2 and consequently the speed of rotation of sprocket-ring 92 must always be greater than or equal to the speed of rotation of shaft 27 i.e. of the spool 2.

The ratchet-motion 94 comprises a centre part or hub 95 connected to shaft 27 and having ramps 96 which, in cooperation with the cylindrical inside face of sprocket-ring 92, form cavities whose height is tapering off. Into these cavities are inserted balls 97 the diameter of which is less than the maximum height of the cavities. The ramps 96 on centre part 95 terminate in radial walls 98 containing sprung plungers 99 which force the balls 97 in the direction of the tapers.

It should be noted that other known types of equivalent one-way coupling devices may be used, such as those using a ratchet and a pawl or those with use springs, for example.

The operation of the film-feeding or unwinding device is as follows: when the film F is unrolled from spool 2 being drawn therefrom by means of roller 3, it in turn rotates spool 2. Spool 2, which is coupled via fork 28 to shaft 27, only drives the centre part 95 when the sprocket-ring 92 driven by sprocket-wheel 90 and chain 93, is turning at a greater speed than spool 2. In the reverse case, or when the sprocket-ring 92 is slowed down or stopped by operating brake 91, the balls are thrust towards the taper in the cavity between the ring-gear 92 and the ramp 96 and lock, thus coupling sprocket-ring 92 to centre part 95. When the shaft 22 is braked abruptly to a halt, the kinetic energy stored in the spool 2 causes the centre part 95 to rebound against the balls 97 and brings about a rotary movement in the opposite direction until the film F is tensioned between spool 2 and the feeding rollers 3 and 4.

To ensure correct operation, it is necessary to drive ring-gear 92 at a speed greater than the maximum speed of spool 2. To this end, the transmission formed by sprocket-wheel 90, chain 93 and sprocket-ring 92 is geared up in a suitable ratio.

FIG. 5 is a cross-section along line CC' of an embodiment of the coupling device 94 in FIG. 4.

In this case the sprocket-ring 92 is seated by means of bearings 86 in the rear wall of the magazine containing spool 2. A shaft 271 is seated within the annular gear by means of a ball-race 87. The centre part or hub 95 is fitted over shaft 271 and is held in place by a screw 272 which extends into a point which fits into a hole in the centre of spool 2. Fork 280 is mounted on shaft 271 by means of a key 281 and is thrust towards the spool by a spring 282. The rachet-motion 94 is inserted between the sprocket-ring 92 and the shaft 271 as shown in FIG. 4 and as explained above.

FIGS. 6 and 7 are schematic views of two different embodiments of an X-ray diagnostic apparatus which includes a film-handling arrangement according to the invention.

In FIG. 6 is shown an X-ray diagnostic apparatus having an arm (not shown) which carries a fixed X-ray tube which is so arranged that the centre of the beam is always directed onto the centre of the maximum area of the exposure fiels C, preferably perpendicular to the plane of the film, the focal distance remaining at a constant value. The X-ray beam whose intensity is made uniform by means of a wedge shaped filter 102, is cut down to the size of the film by means of a diaphragm 103, the position of which is controlled to correspond to that of the leaded mask 19. To this end, the shaft of one of the pulleys 40 which move the strip 41 (and the mask 19) via belts 38 is coupled to the shaft of a first angle indicating device 100, such as a potentiometer, which generates signals which are a function of the angular position of its shaft. A movable diaphragm 103 is slideably mounted on the protective casing of for the tube (not shown) below the wedge filter 102, this diaphragm 103 being operated by, for example, a rack 104 secured to it and a pinion secured to the shaft of a motor 106. This shaft is coupled to the shaft of a second angle indicating device 107 similar to the first 100, these two indicator devices 100 and 107 feeding a conventional differential servo-amplifier and computer circuit 108, which in turn feeds the motor 106 so that the diaphragm 103 will restrict the extent of the irradiated area to the area of the film, i.e. so that the diaphragm will move proportionally to the movement of mask 19.

In FIG. 7 is schematically shown an X-ray diagnostic apparatus in which an X-ray source carrying column 109 is movable in parallel to the plane of the film so that the centre of the beam is always directed onto the centre of the film format which is selected by moving the mask 19, it preferably being possible to alter the focal distance as a function of this format.

Column 109 is mounted on a carriage 110, which moves on rails 111 fixed to the framework of the film-handling arrangement and is driven by means of a drive mechanism consisting of a motor 112, two pulleys 113, 114 and an endless belt 115 to which column 109 is secured at 116. A tube-carrying arm 117 perpendicular to column 109 is so mounted as to be able to move along column 109. The mechanism for moving arm 117 is represented by a threaded rod 118 which is driven in rotation by an electric motor 119 and by a threaded bore in lug 120 attached to arm 117.

The shaft of motor 112 is coupled to the shaft of a third angle indicator device 121 and the shaft of motor 119 is coupled to the shaft of a fourth angle indicator device 122, these devices 121 and 122 being similar to the first device 100 in FIG. 6. The motor 112, which positions the column 109 at half the length of the selected format, makes the column 109 move in parallel to and in the same direction as the leaded mask, but of half the distance. This is achieved by means of a first conventional computing and servo-amplifier circuit 123, which is fed by devices 100 and 121 and which controls motor 123. Since the focal distance is likewise a linear function of the format length selected, the position of the arm 117 along column 109 is controlled by means of a second conventional computing and servo-amplifier circuit 124 as a function of the signal supplied by angle indicator devices 121 and 122 which indicate respectively the position of column 109 along the exposure field and the position of arm 117 along column 109.

It should be noted that it is possible to control the respective positions of column 109 and of the tube-carrying arm 117 as a function of the position of the end of the leaded mask 19 using other conventional means such as transmissions which employ chains and/or gears coupled to the shaft of motor 37. It is also possible to fit a rack (not shown) parallel to the direction in which the film is fed and to mount a single motor on column 109 which drives a pinion (not shown) which meshes with the fixed rack. The single motor which displaces the tube-carrying column 109 drives a device which generates signals for control purposes and also, by means of conventional transmissions (a threaded shaft, a chain or some other means) drives a carriage attached to the tube-carrying arm 117 along column 109. In this case, it is only necessary to provide a single servo-amplifier circuit, the focal distance being a proportional and unambiguous function of format i.e. of the position of column 109.

What we claim is:

1. An X-ray film-handling arrangement using roll-film, comprising: means for supplying film from a roll including a first pair of contiguous feeding rollers driven by a first motor; means for transferring the film including two pairs of flat superposed and contiguous conveyor belts respectively stretched on a second and a third pair of transfer rollers driven by a second motor, the two pairs of belts being so arranged as to grip the lateral edges of the film, said second motor having a shaft coupled, by means of a clutch to one of said second pair of transfer rollers whose shaft being provided with a brake; means for cutting said film including a pair of blades arranged between said supplying means and said transferring means to cut the film when it has been transferred to its the exposure position; and a movable member including a leaded mask displaceable by means of a third motor for limiting the length of the film format being irradiated to any length whatsoever between predetermined maximum and minimum lengths; and means for reproducing the displacement of the film including an indexing belt held in parallel with the conveyor belts on a pair of pulleys respectively located beyond the extreme positions of the said movable member, one of said pulleys being coupled to the shaft of said second motor so that a random point on the indexing belt can be moved for a distance identical to the length of film which is transferred by said conveyor belts, said indexing belt being provided with a marker for co-operating with at least one detection device secured to the end of said movable member, said detection device delivering a first electrical control signal, when the said marker passes adjacent thereto, transmitted to the said clutch and/or brake for controlling the displacements of said conveyor belts, to stop said latter when the end of the film reaches that of the movable member.

2. An arrangement as claimed in claim 1, further provided with a magazine to store exposed film including a parallelepiped light-proof casing provided with an elongated slot through which the exposed film is inserted therein, and within the said casing: a central cylinder roller; four peripheral rollers which are arranged in respective corners of the casing parallel to said slot; a movable roller having a shaft movably mounted in a pair of curvilinear seatings and urged towards said central roller by elastic means; two or more parallel belts tended in such a way that one of their faces passes around said central roller and the other one of their faces passes around each of the said peripheral rollers and the movable roller, one of said peripheral rollers having a shaft coupled to one of the transfer rollers adjacent said magazine, to drive the magazine belts at substantially the same speed as the said conveyor belts, the exposed film being stored between the belts and the central roller.

3. An arrangement as claimed in claim 1, of the type in which the unexposed film is wound on a spool, wherein the shaft of said first motor driving the feeding rollers is further coupled to a rotary element rotating in the same direction as the said spool, at a speed higher than the maximum speed of rotation of the latter while the film is unrolled, said spool being coupled to a shaft coupled, in its turn, to said rotary element by a unidirectional coupling device, whereby allowing said spool to turn relatively to said element only in the direction opposite to the direction of rotation for which the film is unwound from said spool.

4. An X-ray diagnostic apparatus including an arrangement as claimed in claim 1, wherein said apparatus further includes an X-ray tube carrying arrangement for holding the X-ray tube in a fixed position and, adjacent to the X-ray tube, a movable diaphragm for limiting the X-ray beam having its position controlled by a fourth motor fed by means of a servo-amplifier circuit, said position being made to correspond to that of the said movable member, so as to match the area of the irradiated field to the variable length of the film.

5. An X-ray diagnostic apparatus including an arrangement as claimed in claim 1, wherein said apparatus further includes: a tube-carrying column mounted on said arrangement for displacements parallel to the direction of the film motion in the exposure field; an arm for carrying an X-ray tube mounted on and movable along said column, the position of the column relatively to the film and of the arm along the column being controlled to correspond to the position of the movable member, whereby to direct the central ray of the X-ray beam onto the centre of the film format selected by means of said movable member and to limit the area of the irradiated field to a length appropriate to this format.

* * * * *